United States Patent
Liu et al.

(10) Patent No.: US 8,206,843 B2
(45) Date of Patent: Jun. 26, 2012

(54) BIOCERAMIC COATING, METHOD OF MAKING AND USE THEREOF

(75) Inventors: Qibin Liu, Guizhou (CN); Wenfei Li, Guizhou (CN); Ling Wu, Guizhou (CN)

(73) Assignee: Guizhou University, Guizhou (CN)

( * ) Notice: Subject to any disclaimer, the term of this patent is extended or adjusted under 35 U.S.C. 154(b) by 423 days.

(21) Appl. No.: 12/252,958

(22) Filed: Oct. 16, 2008

(65) Prior Publication Data

US 2009/0228115 A1    Sep. 10, 2009

(30) Foreign Application Priority Data

May 16, 2007 (CN) ............... 2006 1 0201016
May 16, 2007 (CN) ............... 2007 1 0200627
May 16, 2007 (CN) ............... 2007 1 0200631
May 16, 2007 (CN) ............... 2007 1 0200632

(51) Int. Cl.
*B32B 15/04* (2006.01)
*A61F 2/02* (2006.01)

(52) U.S. Cl. ............ 428/701; 428/472.3; 428/702; 623/23.56; 623/23.57; 623/23.72

(58) Field of Classification Search ............ 428/701, 428/702, 472.3; 623/23.56, 23.57, 23.6, 623/23.72
See application file for complete search history.

(56) References Cited

FOREIGN PATENT DOCUMENTS

| CN | 1654433 A | 8/2005 |
|---|---|---|
| CN | 101053675 A | 10/2007 |
| CN | 101053676 A | 10/2007 |
| CN | 101053677 A | 10/2007 |
| CN | 101053678 A | 10/2007 |

OTHER PUBLICATIONS

English machine translation CN 1654433.*

* cited by examiner

*Primary Examiner* — Timothy Speer
*Assistant Examiner* — Lauren Robinson
(74) *Attorney, Agent, or Firm* — Ping Wang; Andrews Kurth, LLP

(57) ABSTRACT

Disclosed are a gradient bioceramic coating comprising a rare earth oxide, a broadband laser method for preparing the bioceramic coating, and the use of the bioceramic coating in the field of medical materials.

6 Claims, No Drawings

US 8,206,843 B2

BIOCERAMIC COATING, METHOD OF MAKING AND USE THEREOF

RELATED APPLICATIONS

The present application is based on the Chinese application Nos. 200710200627.1, 200710200631.8, 200710200632.2 and 200710200628.6, published on Oct. 17, 2007, which are explicitly incorporated herein by reference in its entirety.

BACKGROUND OF THE INVENTION

1. Field of the Invention

The present application is directed to a bioceramic coating, a method of making and use thereof. In particular, the present application is directed to a gradient bioceramic coating comprising a rare earth oxide, a broadband laser method for preparing the bioceramic coating and the use of the bioceramic coating in the field of medical materials.

2. Description of the Related Art

Bioceramic coating is an important part of biomedical materials and plays an important role in restoring defects of human sclerous tissues and rebuilding the lost physiological functions. Generally, there are two kinds of techniques of preparing bioactive ceramic coatings, i.e., dry process and wet process. The dry process is meant to carry out various reactions and depositions in gas phase. Examples of the dry process include plasma spraying, physical vapor deposition, chemical vapor deposition, thermal spraying, laser cladding, ion injection, and the like. The wet process is a technique that utilizes various reactions carried out in liquid phase so as to deposit a coating on a substrate. Examples of wet process include sol-gel method, electrochemical deposition, self-assembling monolayer film method, and the like.

Laser cladding method is a technique which comprises precoating a mixed powder of $CaHPO_4 \cdot 2H_2O$ and $CaCO_3$ with a certain proportion on the surface of the substrate, and then cladding treating the surface of the metal substrate with a $CO_2$ laser processing system so that synthesis and coating of hydroxyapatite (HA) on the surface of titanium alloy are completed in one step.

The mechanical properties of HA bioceramic coating mainly depends on the sintering density and microstructure of the final sintered product. The technological parameters of broadband laser cladding can have a significant effect on the microstructure and sinterability of the bioceramic coating.

BRIEF SUMMARY OF THE INVENTION

In a first aspect, the present application is directed to a gradient bioceramic coating, wherein the gradient bioceramic coating is prepared with powdery titanium and powdery composite ceramics, wherein the powdery composite ceramics are composed of powdery ceramics obtained by mixing $CaHPO_4 \cdot 2H_2O$ and $CaCO_3$, and a rare earth oxide added into the powdery ceramics.

In a second aspect, the present application is directed to a gradient bioceramic coating, wherein the gradient bioceramic coating is prepared with powdery titanium, powdery composite ceramics and hydroxyapatite, wherein the powdery composite ceramics are composed of powdery ceramics obtained by mixing $CaHPO_4 \cdot 2H_2O$ and $CaCO_3$, and a rare earth oxide added into the powdery ceramics.

In a third aspect, the present application is directed to a method of making a gradient bioceramic coating, comprising (a) mixing and grinding powdery ceramics and a rare earth oxide to give a first mixture, and then mixing and grinding the first mixture and powdery titanium to give a coating powder;

(b) mixing the coating powder and an adhesive to give a second mixture, and then prepressing the second mixture on the surface of a titanium alloy TC4; and (c) with broadband laser cladding techniques, cladding a first gradient layer on the surface of the titanium alloy TC4, and then prepressing the coating powders on the surface of the titanium alloy TC4 and cladding a second gradient layer, and then prepressing the coating powders on the surface of the titanium alloy TC4 again and cladding a third gradient layer, so as to obtain the gradient bioceramics on the surface of the titanium alloy TC4.

In a fourth aspect, the present application is directed to a gradient bioceramic coating, the gradient bioceramic coating is made according to a method comprising (a) mixing and grinding powdery ceramics and a rare earth oxide to give a first mixture, and then mixing and grinding the first mixture and powdery titanium to give a coating powder;

(b) mixing the coating powder and an adhesive to give a second mixture, and then prepressing the second mixture on the surface of a titanium alloy TC4; and (c) with broadband laser cladding techniques, cladding a first gradient layer on the surface of the titanium alloy TC4, and then prepressing the coating powders on the surface of the titanium alloy TC4 and cladding a second gradient layer, and then prepressing the coating powders on the surface of the titanium alloy TC4 again and cladding a third gradient layer, so as to obtain the gradient bioceramics on the surface of the titanium alloy TC4.

In a fifth aspect, the present application is directed to use of a gradient bioceramic coating in defect-restoration and substitution of human sclerous tissues.

DETAILED DESCRIPTION OF THE INVENTION

In the following description, certain specific details are included to provide a thorough understanding of various disclosed embodiments. One skilled in the relevant art, however, will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, which is as "including, but not limited to".

Reference throughout this specification to "one embodiment", or "an embodiment", or "in another embodiment", or "some embodiments", or "in some embodiments" means that a particular referent feature, structure, or characteristic described in connection with the embodiment is included in at least one embodiment. Thus, the appearance of the phrases "in one embodiment", or "in an embodiment", or "in another embodiment", or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a", "an", and "the" include plural referents unless the content clearly dictates otherwise. Thus, for example, reference to a solvent containing "a substance having polyhydroxy and/or polyamino groups" includes a single substance having polyhydroxy and/ or polyamino groups, or two or more substances having polyhydroxy and/or polyamino groups. It should also be noted that the term "or" is generally employed in its sense including "and/or" unless the content clearly dictates otherwise.

In one aspect, the present application is directed to a gradient bioceramic coating, wherein the gradient bioceramic coating is prepared with powdery titanium and powdery composite ceramics, wherein the powdery composite ceramics are composed of powdery ceramics obtained by mixing $CaHPO_4.2H_2O$ and $CaCO_3$, and a rare earth oxide added into the powdery ceramics.

In some embodiments, on the basis of weight percent, the gradient bioceramic coating is prepared with about 60 to 0% of powdery titanium and about 40 to 100% of powdery composite ceramics, wherein the powdery composite ceramics are composed of powdery ceramics obtained by mixing about 67 to 85% by weight of $CaHPO_4.2H_2O$ and about 15 to 33% by weight of $CaCO_3$, and about 0.2 to 1.0% by weight of a rare earth oxide added into the powdery ceramics.

In some embodiments, on the basis of weight percent, the gradient bioceramic coating is prepared with about 80 to 10% of powdery titanium and about 20 to 90% of powdery composite ceramics, wherein the powdery composite ceramics are composed of powdery ceramics obtained by mixing about 67 to 85% by weight of $CaHPO_4.2H_2O$ and about 15 to 33% by weight of $CaCO_3$, and about 0.2 to 1.0% by weight of a rare earth oxide added into the powdery ceramics.

In some embodiments, the particle size of the powdery titanium is in the range of about 10 to 90 µm, the particle size of the powdery composite ceramics is in the range of about 20 to 60 µm, and the particle size of the rare earth oxide is in the range of about 0.1 to 10 µm.

In some embodiments, the particle size of the powdery titanium is in the range of about 20 to 80 µm, the particle size of the powdery composite ceramics is in the range of about 30 to 50 µm, and the particle size of the rare earth oxide is in the range of about 1 to 5 µm.

In some preferred embodiments, the particle size of the powdery titanium is about 40 µm, the particle size of the powdery composite ceramics is about 36 µm, and the particle size of the rare earth oxide is about 4 µm.

In some preferred embodiments, the particle size of the powdery titanium is about 20 µm, the particle size of the powdery composite ceramics is about 30 µm, and the particle size of the rare earth oxide is about 1 µm.

In some preferred embodiments, the particle size of the powdery titanium is about 80 µm, the particle size of the powdery composite ceramics is about 50 µm, and the particle size of the rare earth oxide is about 5 µm.

In some embodiments, the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics.

In some preferred embodiments, the powdery composite ceramics are composed of powdery ceramics obtained by mixing about 72% by weight of $CaHPO_4.2H_2O$ and about 28% by weight of $CaCO_3$, and about 0.4% by weight of a rare earth oxide added into the powdery ceramics.

In some preferred embodiments, the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics.

In some preferred embodiments, the powdery composite ceramics are composed of powdery ceramics obtained by mixing about 80% by weight of $CaHPO_4.2H_2O$ and about 20% by weight of $CaCO_3$, and about 0.8% by weight of a rare earth oxide added into the powdery ceramics.

Rare earth elements are a generic name of scandium, yttrium, and lanthanoid in Group IIIB of the Periodic Table of the Elements, which include scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu), wherein promethium is an artificial radioactive element.

In general, lanthanum, cerium, praseodymium, neodymium, promethium, samarium and europium are called light rare earth elements, while gadolinium, terbium, dysprosium, holmium, erbium, thulium, ytterbium and lutetium are called heavy rare earth elements. Light rare earth elements have greater antithrombotic effects than those heavy earth elements have. The radius of a light rare earth ion is closer to the radius of a calcium ion than that of a heavy rare earth ion. A rare earth ion has one more positive charge than a calcium ion does. When a calcium ion is substituted by a rare earth ion, rare earth ions effectively and competitively inhibits the effects of calcium ions during the blood coagulation process.

In some embodiments, a rare earth oxide that can be used in the present application includes, but is not limited to, yttrium oxide ($Y_2O_3$), yttrium europium oxide (($Y,Eu)_2O_3$), europium oxide ($Eu_2O_3$), lanthanum oxide ($La_2O_3$), cerous oxide ($Ce_2O_3$), ceric oxide ($CeO_2$), terbium oxide ($Tb_4O_7$) (including cerium terbium oxide (($Ce, Tb)_xO_y$), lanthanum cerium terbium oxide (($La, Ce, Tb)_xO_y$), lanthanum phosphate activated by cerium and terbium: Ce(III), Tb(III)), samarium oxide ($Sm_2O_3$), neodminu oxide ($Nd_2O_3$), dysprosium oxide ($Dy_2O_3$), erbium oxide ($Er_2O_3$), ytterbium oxide ($Yb_2O_3$) and cerium zirconium oxide (($Ce,Zr)O_2$).

In some preferred embodiments, the rare earth oxide is selected from the group consisting of lanthanum oxide ($La_2O_3$), ceric oxide ($CeO_2$) and yttrium oxide ($Y_2O_3$).

In some embodiments, the particle size of the powdery titanium is in the range of about 10 to 90 µm, the particle size of the powdery composite ceramics is in the range of about 20 to 60 µm, and the particle size of the rare earth oxide is in the range of about 0.1 to 10 µm, wherein the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics.

In some preferred embodiments, the particle size of the powdery titanium is in the range of about 20 to 80 µm, the particle size of the powdery composite ceramics is in the range of about 30 to 50 µm, and the particle size of the rare earth oxide is in the range of about 1 to 5 µm, wherein the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics, and wherein the rare earth oxide is selected from the group consisting of lanthanum oxide ($La_2O_3$), ceric oxide ($CeO_2$) and yttrium oxide ($Y_2O_3$).

In some more preferred embodiments, the particle size of the powdery titanium is about 40 µm, the particle size of the powdery composite ceramics is about 36 µm, and the particle size of the rare earth oxide is about 4 µm, wherein the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics, and wherein the rare earth oxide is selected from the group consisting of lanthanum oxide ($La_2O_3$), ceric oxide ($CeO_2$) and yttrium oxide ($Y_2O_3$).

In some more preferred embodiments, the particle size of the powdery titanium is about 40 μm, the particle size of the powdery composite ceramics is about 36 μm, and the particle size of the rare earth oxide is about 4 μm, wherein the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics, and wherein the rare earth oxide is lanthanum oxide ($La_2O_3$).

In some more preferred embodiments, the particle size of the powdery titanium is about 40 μm, the particle size of the powdery composite ceramics is about 36 μm, and the particle size of the rare earth oxide is about 4 μm, wherein the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics, and wherein the rare earth oxide is ceric oxide ($CeO_2$).

In another aspect, the present application is directed to a gradient bioceramic coating, wherein the gradient bioceramic coating is prepared with powdery titanium, powdery composite ceramics and hydroxyapatite, wherein the powdery composite ceramics are composed of powdery ceramics obtained by mixing $CaHPO_4.2H_2O$ and $CaCO_3$, and a rare earth oxide added into the powdery ceramics.

In some embodiments, on the basis of weight percent, the gradient bioceramic coating is prepared with about 60 to 0% of powdery titanium, about 40 to 100% of powdery composite ceramics and about 0 to 50% of hydroxyapatite, wherein the powdery composite ceramics are composed of powdery ceramics obtained by mixing about 67 to 85% by weight of $CaHPO_4.2H_2O$ and about 15 to 33% by weight of $CaCO_3$, and about 0.2 to 1.0% by weight of a rare earth oxide added into the powdery ceramics.

In some embodiments, the particle size of the powdery titanium is in the range of about 10 to 90 μm, the particle size of the powdery composite ceramics is in the range of about 20 to 60 μm, the particle size of the hydroxyapatite is in the range of about 5 to 50 μm, and the particle size of the rare earth oxide is in the range of about 0.1 to 10 μm.

In some embodiments, the particle size of the powdery titanium is in the range of about 20 to 80 μm, the particle size of the powdery composite ceramics is in the range of about 30 to 50 μm, the particle size of the hydroxyapatite is in the range of about 1 to 30 μm, and the particle size of the rare earth oxide is in the range of about 1 to 5 μm.

In some preferred embodiments, the particle size of the powdery titanium is about 40 μm, the particle size of the powdery composite ceramics is about 36 μm, the particle size of the hydroxyapatite is about 15 μm, and the particle size of the rare earth oxide is about 4 μm.

In some preferred embodiments, the particle size of the powdery titanium is about 20 μm, the particle size of the powdery composite ceramics is about 30 μm, the particle size of the hydroxyapatite is about 10 μm, and the particle size of the rare earth oxide is about 1 μm.

In some preferred embodiments, the particle size of the powdery titanium is about 80 μm, the particle size of the powdery composite ceramics is about 50 μm, the particle size of the hydroxyapatite is about 30 μm, and the particle size of the rare earth oxide is about 5 μm.

In some embodiments, the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics.

In some preferred embodiments, the powdery composite ceramics are composed of powdery ceramics obtained by mixing about 72% by weight of $CaHPO_4.2H_2O$ and about 28% by weight of $CaCO_3$, and about 0.4% by weight of a rare earth oxide added into the powdery ceramics.

In some preferred embodiments, the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics.

In some preferred embodiments, the powdery composite ceramics are composed of powdery ceramics obtained by mixing about 80% by weight of $CaHPO_4.2H_2O$ and about 20% by weight of $CaCO_3$, and about 0.8% by weight of a rare earth oxide added into the powdery ceramics.

In some embodiments, a rare earth oxide that can be used in the present application includes, but is not limited to, yttrium oxide ($Y_2O_3$), yttrium europium oxide (($Y,Eu)_2O_3$), europium oxide ($Eu_2O_3$), lanthanum oxide ($La_2O_3$), cerous oxide ($Ce_2O_3$), ceric oxide ($CeO_2$), terbium oxide ($Tb_4O_7$) (including cerium terbium oxide (($Ce, Tb)_xO_y$), lanthanum cerium terbium oxide (($La, Ce, Tb)_xO_y$), lanthanum phosphate activated by cerium and terbium: $Ce(III)$, $Tb(III)$), samarium oxide ($Sm_2O_3$), neodminu oxide ($Nd_2O_3$), dysprosium oxide ($Dy_2O_3$), erbium oxide ($Er_2O_3$), ytterbium oxide ($Yb_2O_3$) and cerium zirconium oxide (($Ce,Zr)O_2$).

In some preferred embodiments, the rare earth oxide is selected from the group consisting of lanthanum oxide ($La_2O_3$), ceric oxide ($CeO_2$) and yttrium oxide ($Y_2O_3$).

In some embodiments, the particle size of the powdery titanium is in the range of about 10 to 90 μm, the particle size of the powdery composite ceramics is in the range of about 20 to 60 μm, the particle size of the hydroxyapatite is in the range of about 5 to 50 μm, and the particle size of the rare earth oxide is in the range of about 0.1 to 10 μm, wherein the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics.

In some preferred embodiments, the particle size of the powdery titanium is in the range of about 20 to 80 μm, the particle size of the powdery composite ceramics is in the range of about 30 to 50 μm, the particle size of the hydroxyapatite is in the range of about 1 to 30 μm, and the particle size of the rare earth oxide is in the range of about 1 to 5 μm, wherein the powdery composite ceramics are composed of powdery ceramics obtained by mixing about 72 to 80% by weight of $CaHPO_4.2H_2O$ and about 20 to 28% by weight of $CaCO_3$, and about 0.4 to 0.8% by weight of a rare earth oxide added into the powdery ceramics, and wherein the rare earth oxide is selected from the group consisting of lanthanum oxide ($La_2O_3$), ceric oxide ($CeO_2$) and yttrium oxide ($Y_2O_3$).

In some more preferred embodiments, the particle size of the powdery titanium is about 40 μm, the particle size of the powdery composite ceramics is about 36 μm, the particle size of the hydroxyapatite is about 15 μm, and the particle size of the rare earth oxide is about 4 μm, wherein the powdery composite ceramics are composed of powdery ceramics obtained by mixing about 78% by weight of $CaHPO_4.2H_2O$ and about 22% by weight of $CaCO_3$, and about 0.6% by weight of a rare earth oxide added into the powdery ceramics, and wherein the rare earth oxide is selected from the group consisting of lanthanum oxide ($La_2O_3$), ceric oxide ($CeO_2$) and yttrium oxide ($Y_2O_3$).

In other aspects, the present application is directed to a method of making a gradient bioceramic coating, comprising
  (a) mixing and grinding powdery ceramics and a rare earth oxide to give a first mixture, and then mixing and grinding the first mixture and powdery titanium to give a coating powder;
  (b) mixing the coating powder and an adhesive to give a second mixture, and then prepressing the second mixture on the surface of a titanium alloy TC4; and
  (c) with broadband laser cladding techniques, cladding a first gradient layer on the surface of the titanium alloy TC4, and then prepressing the coating powders on the surface of the titanium alloy TC4 and cladding a second gradient layer, and then prepressing the coating powders on the surface of the titanium alloy TC4 again and cladding a third gradient layer, so as to obtain the gradient bioceramics on the surface of the titanium alloy TC4.

In some embodiments, the method of making a gradient bioceramic coating further comprises mixing and grinding the coating powder obtained in step (a) and hydroxyapatite before carrying out the step (b) of mixing with an adhesive.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 10 to 40% by weight of powdery titanium and about 90 to 60% by weight of powdery composite ceramics, and a third gradient layer is prepared with about 100% by weight of powdery composite ceramics.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 20 to 40% by weight of powdery titanium and about 80 to 60% by weight of powdery composite ceramics, and a third gradient layer is prepared with about 100% by weight of powdery composite ceramics.

In some preferred embodiments, a first gradient layer prepressed on the surface of the titanium alloy TC4 is prepared with about 60% by weight of powdery titanium and about 40% by weight of powdery composite ceramics, a second gradient layer is prepared with about 30% by weight of powdery titanium and about 70% by weight of powdery composite ceramics, and a third gradient layer is prepared with about 50% by weight of hydroxyapatite and about 50% by weight of powdery composite ceramics.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 20 to 40% by weight of powdery titanium and about 80 to 60% by weight of powdery composite ceramics, and a third gradient layer is prepared with about 40 to 60% by weight of hydroxyapatite and about 60 to 40% by weight of powdery composite ceramics.

In some preferred embodiments, a first gradient layer prepressed on the surface of the titanium alloy TC4 is prepared with about 60% by weight of powdery titanium and about 40% by weight of powdery composite ceramics, a second gradient layer is prepared with about 30% by weight of powdery titanium and about 70% by weight of powdery composite ceramics, and a third gradient layer is prepared with about 50% by weight of hydroxyapatite and about 50% by weight of powdery composite ceramics.

In some embodiments, a first gradient layer prepressed on the surface of the titanium alloy TC4 is prepared with about 60 to 80% by weight of powdery titanium and about 40 to 20% by weight of powdery composite ceramics, a second gradient layer is prepared with about 30 to 50% by weight of powdery titanium and about 70 to 50% by weight of powdery composite ceramics, and a third gradient layer is prepared with about 5 to 15% by weight of powdery titanium and about 95 to 85% by weight of powdery composite ceramics.

In some preferred embodiments, a first gradient layer prepressed on the surface of the titanium alloy TC4 is prepared with about 70% by weight of powdery titanium and about 30% by weight of powdery composite ceramics, a second gradient layer is prepared with about 40% by weight of powdery titanium and about 60% by weight of powdery composite ceramics, and a third gradient layer is prepared with about 10% by weight of powdery titanium and about 90% by weight of powdery composite ceramics.

In some embodiments, the thickness of the coating layer prepressed on the surface of the titanium alloy TC4 is in the range of about 0.2 to 0.8 mm.

In some embodiments, the thickness of the coating layer prepressed on the surface of the titanium alloy TC4 is in the range of about 0.4 to 0.6 mm.

In some embodiments, the thicknesses of a first gradient layer, a second gradient layer and a third gradient layer prepressed on the surface of the titanium alloy TC4 may be identical or different.

In some preferred embodiments, all the thicknesses of a first gradient layer, a second gradient layer and a third gradient layer prepressed on the surface of the titanium alloy TC4 are 0.4 mm.

In some preferred embodiments, all the thicknesses of a first gradient layer, a second gradient layer and a third gradient layer prepressed on the surface of the titanium alloy TC4 are 0.5 mm.

In some preferred embodiments, all the thicknesses of a first gradient layer, a second gradient layer and a third gradient layer prepressed on the surface of the titanium alloy TC4 are 0.6 mm.

In some embodiments, the powdery composite ceramics and the rare earth oxide are mixed and ground over about 1 to 5 hours.

In some embodiments, the powdery composite ceramics and the rare earth oxide are mixed and ground over about 1 to 5 hours to give a first mixture, and the first mixture and powdery titanium are mixed and ground over about 1 to 5 hours to give a coating powder.

In some embodiments, the technological parameters of broadband laser cladding are about 2.0 to 3.0 kW of output power P, about 100 to 200 mm/min of scanning rate V, and about 16 to 30 mm×1 to 4 mm of spot size D.

In some preferred embodiments, the technological parameters of broadband laser cladding are about 2.5 kW of output power P, about 150 mm/min of scanning rate V, and about 16 mm×2 mm of spot size D.

In some embodiments, the pressure used in prepressing the coating powders is in the range of about 40 to 60 kg/cm$^2$.

In some preferred embodiments, the pressure used in prepressing the coating powders is about 50 kg/cm$^2$.

In some embodiments, the apparatuses used in the broadband laser cladding are TJ-HL-5000 5 kW $CO_2$ lasers, TJ-LTM-VI five-axis three axes linkage laser processing numerical control machine, and JKF-6 laser broadband scan mirror.

In some embodiments, an adhesive that can be used in the present application includes, but is not limited to, chemical adhesives and bioadhesives.

Exemplary chemical adhesives include, but are not limited to, α-cyanoacrylates adhesives; polyurethanes adhesives; gelatins, such as GRF adhesives; organosilicons adhesives;

alkyd esters adhesives, such as soya alkyds adhesives; poly (hydroxyethyl methacrylate) adhesives; polyvinyl emulsion adhesives; collodions adhesives; and the like.

Exemplary bioadhesives include, but are not limited to, those biomolecules that mediate attachment of cells, tissue, organs or organisms onto non-biological surfaces like glass, rock etc. This group of biomolecules includes marine mussel adhesive proteins, fibrin-like proteins, spider-web proteins, plant-derived adhesives (resins), adhesives extracted from marine animals, and insect-derived adhesives (like resilins). Some specific examples of adhesives are: Fibrin; fibroin; *Mytilus edulis* foot protein (mefp1, "mussel adhesive protein"); other mussel's adhesive proteins; proteins and peptides with glycine-rich blocks; proteins and peptides with poly-alanine blocks; and silks.

In some preferred embodiments, the adhesives used in the present application are alkyd esters adhesives.

In some more preferred embodiments, the adhesives used in the present application are soya alkyds.

In some even more preferred embodiments, the adhesives used in the present application are about 1 to 5 mL of soya alkyds.

In another aspect, the present application is directed to a gradient bioceramic coating, the gradient bioceramic coating is made according to a method comprising
  (a) mixing and grinding powdery ceramics and a rare earth oxide to give a first mixture, and then mixing and grinding the first mixture and powdery titanium to give a coating powder;
  (b) mixing the coating powder and an adhesive to give a second mixture, and then prepressing the second mixture on the surface of a titanium alloy TC4; and
  (c) with broadband laser cladding techniques, cladding a first gradient layer on the surface of the titanium alloy TC4, and then prepressing the coating powders on the surface of the titanium alloy TC4 and cladding a second gradient layer, and then prepressing the coating powders on the surface of the titanium alloy TC4 again and cladding a third gradient layer, so as to obtain the gradient bioceramics on the surface of the titanium alloy TC4.

In some embodiments, the method of making a gradient bioceramic coating further comprises mixing and grinding the coating powder obtained in step (a) and hydroxyapatite before carrying out the step (b) of mixing with an adhesive.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 10 to 40% by weight of powdery titanium and about 90 to 60% by weight of powdery composite ceramics, and a third gradient layer is prepared with about 100% by weight of powdery composite ceramics.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 20 to 40% by weight of powdery titanium and about 80 to 60% by weight of powdery composite ceramics, and a third gradient layer is prepared with about 100% by weight of powdery composite ceramics.

In some preferred embodiments, a first gradient layer prepressed on the surface of the titanium alloy TC4 is prepared with about 60% by weight of powdery titanium and about 40% by weight of powdery composite ceramics, a second gradient layer is prepared with about 30% by weight of powdery titanium and about 70% by weight of powdery composite ceramics, and a third gradient layer is prepared with about 50% by weight of hydroxyapatite and about 50% by weight of powdery composite ceramics.

In some embodiments, a first gradient layer prepressed on the surface of the titanium alloy TC4 is prepared with about 50 to 70% by weight of powdery titanium and about 50 to 30% by weight of powdery composite ceramics, a second gradient layer is prepared with about 20 to 40% by weight of powdery titanium and about 80 to 60% by weight of powdery composite ceramics, and a third gradient layer is prepared with about 40 to 60% by weight of hydroxyapatite and about 60 to 40% by weight of powdery composite ceramics.

In some preferred embodiments, a first gradient layer prepressed on the surface of the titanium alloy TC4 is prepared with about 60% by weight of powdery titanium and about 40% by weight of powdery composite ceramics, a second gradient layer is prepared with about 30% by weight of powdery titanium and about 70% by weight of powdery composite ceramics, and a third gradient layer is prepared with about 50% by weight of hydroxyapatite and about 50% by weight of powdery composite ceramics.

In some embodiments, a first gradient layer prepressed on the surface of the titanium alloy TC4 is prepared with about 60 to 80% by weight of powdery titanium and about 40 to 20% by weight of powdery composite ceramics, a second gradient layer is prepared with about 30 to 50% by weight of powdery titanium and about 70 to 50% by weight of powdery composite ceramics, and a third gradient layer is prepared with about 5 to 15% by weight of powdery titanium and about 95 to 85% by weight of powdery composite ceramics.

In some preferred embodiments, a first gradient layer prepressed on the surface of the titanium alloy TC4 is prepared with about 70% by weight of powdery titanium and about 30% by weight of powdery composite ceramics, a second gradient layer is prepared with about 40% by weight of powdery titanium and about 60% by weight of powdery composite ceramics, and a third gradient layer is prepared with about 10% by weight of powdery titanium and about 90% by weight of powdery composite ceramics.

In some embodiments, the thickness of the coating layer prepressed on the surface of the titanium alloy TC4 is in the range of about 0.2 to 0.8 mm.

In some embodiments, the thickness of the coating layer prepressed on the surface of the titanium alloy TC4 is in the range of about 0.4 to 0.6 mm.

In some embodiments, the thicknesses of a first gradient layer, a second gradient layer and a third gradient layer prepressed on the surface of the titanium alloy TC4 may be identical or different.

In some preferred embodiments, all the thicknesses of a first gradient layer, a second gradient layer and a third gradient layer prepressed on the surface of the titanium alloy TC4 are 0.4 mm.

In some preferred embodiments, all the thicknesses of a first gradient layer, a second gradient layer and a third gradient layer prepressed on the surface of the titanium alloy TC4 are 0.5 mm.

In some preferred embodiments, all the thicknesses of a first gradient layer, a second gradient layer and a third gradient layer prepressed on the surface of the titanium alloy TC4 are 0.6 mm.

In some embodiments, the powdery composite ceramics and the rare earth oxide are mixed and ground over about 1 to 5 hours.

In some embodiments, the powdery composite ceramics and the rare earth oxide are mixed and ground over about 1 to 5 hours to give a first mixture, and the first mixture and powdery titanium are mixed and ground over about 1 to 5 hours to give a coating powder.

In some embodiments, the technological parameters of broadband laser cladding are about 2.0 to 3.0 kW of output power P, about 100 to 200 mm/min of scanning rate V, and about 16 to 30 mm×1 to 4 mm of spot size D.

In some preferred embodiments, the technological parameters of broadband laser cladding are about 2.5 kW of output power P, about 150 mm/min of scanning rate V, and about 16 mm×2 mm of spot size D.

In some embodiments, the pressure used in prepressing the coating powders is in the range of about 40 to 60 kg/cm$^2$.

In some preferred embodiments, the pressure used in prepressing the coating powders is about 50 kg/cm$^2$.

In some embodiments, the apparatuses used in the broadband laser cladding are TJ-HL-5000 5 kW CO$_2$ lasers, TJ-LTM-VI five-axis three axes linkage laser processing numerical control machine, and JKF-6 laser broadband scan mirror.

In some embodiments, an adhesive that can be used in the present application includes, but is not limited to, chemical adhesives and bioadhesives.

In some preferred embodiments, the adhesives used in the present application are alkyd esters adhesives.

In some more preferred embodiments, the adhesives used in the present application are soya alkyds.

In some even more preferred embodiments, the adhesives used in the present application are about 1 to 5 mL of soya alkyds.

In other aspects, the present application is directed to use of a gradient bioceramic coating in defect-restoration and substitution of human sclerous tissues.

The term "implant" includes within its scope any device intended to be implanted into the body of a vertebrate animal, in particular a mammal such as a human. Non-limiting examples of such devices are medical devices that replaces anatomy or restores a function of the body such as the femoral hip joint; the femoral head; acetabular cup; elbow including stems, wedges, articular inserts; knee, including the femoral and tibial components, stem, wedges, articular inserts or patella components; shoulders including stem and head; wrist; ankles; hand; fingers; toes; vertebrae; spinal discs; artificial joints; dental implants; ossiculoplastic implants; middle ear implants including incus, malleus, stapes, incus-stapes, malleus-incus, malleus-incus-stapes; cochlear implants; orthopaedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices.

In some embodiments, the gradient bioceramics of the present application may be used in restoration of human femoral necrosis, hip joint or tooth defects.

Hereinafter, the invention will be illustrated in more details by the following examples with reference to the drawings for better understanding of various aspects and advantages of the invention. However, it should be understood that the examples below are non-limiting and are only illustrative of some of the embodiments of the present application.

EXAMPLE

Reagents and Apparatus powdery titanium, purity: 95-99.4%, Shanghai Huijing Sub-Nanometer New Materials Co., Ltd.

CaHPO$_4$.2H$_2$O, purity: >99%, Shanghai Rebone Biomaterials Co., Ltd.

CaCO$_3$, purity: >99%, Shanghai Rebone Biomaterials Co., Ltd. rare earth oxides, analytical pure, Shanghai Yuelong New Materials Co., Ltd. hydroxyapatite, purity: >99%, Shanghai Rebone Biomaterials Co., Ltd. titanium alloy TC4, medical titanium materials, Foshan Nanxiang Special Steels Co., Ltd.

soya alkyds, Shanghai Rebone Biomaterials Co., Ltd.

TJ-HL-5000 5 kW CO$_2$ lasers, manufactured by Wuhan Unitylaser Inc.

TJ-LTM-VI five-axis three axes linkage laser processing numerical control machine, manufactured by Tianjin Polytechnic University JKF-6 laser broadband scan mirror, manufactured by Wuhan Unitylaser Inc.

Effects of Contents of Rare Earth Oxide on Phase Structure, Structure and Morphology, and Cracking Sensitivity of Bioceramic Coating The tests were carried out at 0.2%, 0.4%, 0.6%, 0.8% and 1.0% of rare earth oxide, respectively. The test results showed that the content of catalytically synthesized hydroxyapatite and β-calcium phosphate reached the climax when the content of the rare earth oxide was up to 0.4 to 0.6%, while the content of catalytically synthesized hydroxyapatite and β-calcium phosphate began to decrease when the content of the rare earth oxide was up to 0.8%. In conclusion, the content of the rare earth oxide has a significant effect on the formation of bioactive hydroxyapatite and β-calcium phosphate. When the content of the rare earth oxide was up to 0.4 to 0.6%, the content of catalytically synthesized hydroxyapatite and β-calcium phosphate reached the climax. The structure of the bioceramic coating comprising a rare earth oxide is significantly finer than that comprising no rare earth oxide. The fined structure is beneficial to increase the mechanical properties of the bioceramic coating. The cracking sensitivity of the bioceramic coating comprising a rare earth oxide is lower while that comprising no rare earth oxide is higher.

Optimization of Technological Parameters of Broadband Laser Cladding

The studies on thermodynamics and kinetics showed that only by controlling the technological parameters of laser cladding can hydroxyapatite (HA) be formed. Therefore, in order to ensure the effects of the present application, the technological parameters of laser cladding were optimized by inventors.

In order to obtain calcium and phosphor based bioceramic coating comprising HA in the cladding coating and to ensure good bonding between the coating and the substrate, appropriate technological parameters of laser cladding must be chosen.

Upon investigation it has been discovered that controlling a relatively low output power of laser and a relatively high scanning rate are the keys to obtain the bioceramic coating comprising calcium phosphate. However, if the output power is too low or the scanning rate is too high, the substrate and the cladding material will not be melted or will be only partly melted, which leads to an unfirm bonding between the cladding layer and the substrate and therefore affects the bonding strength.

Therefore, in the experiment the optimal technological parameters of laser cladding were determined by changing the output power P and the scanning rate V. In particular, first of all, the spot size D and the scanning rate V were fixed while the output power P was changed. Then the spot size D and the output power P were fixed while the scanning rate V was changed. The optimal technological parameters of laser cladding were determined by analyzing the macro morphology, microstructure and microhardness.

1. Determination of Output Power P

The spot size D and the scanning rate V were fixed while the output power P was changed. First of all, a range of the output power was approximately determined. After several experiments, the range of the broadband laser output power was preliminarily determined as 2.0 to 3.0 kW through carefully observing the bonding conditions of the coating and the substrate and the quality of the coating surface. The test scheme was designed as shown in Table 1.

TABLE 1

Technological Parameters of Broadband Laser Cladding Gradient Bioceramic Coating

| Sample No. | Output Power P (kW) | Scanning Rate V (mm/min) | Spot Size D (mm × mm) |
|---|---|---|---|
| 111 | 2.1 | 145 | 16 × 2 |
| 112 | 2.3 | 145 | 16 × 2 |
| 113 | 2.5 | 145 | 16 × 2 |
| 114 | 2.7 | 145 | 16 × 2 |
| 115 | 2.9 | 145 | 16 × 2 |

(1) Effects of Output Power on Structure of Composite Ceramic Coating

In the present experimental conditions, it was observed that the surface of sample No. 111 prepared with low power exhibits as melted beads and no bioceramic coating was formed. Due to the low output power, laser energy absorbed by unit area of the sample, i.e., specific energy $E_b$ was too low, such that no molten poor was formed on the surface of the titanium alloy. The surface of sample No. 112 was relatively smooth and a bioceramic coating was formed. Bioceramic coatings were also formed on the surfaces of sample Nos. 113-115. However, the surface qualities became worse from sample No. 113 to sample No. 115, in which the surface quality of sample No. 115 was the worst. Due to a gradual increase in the laser output power, laser energy absorbed by unit area of the sample, i.e., specific energy $E_b$ gradually increased too, such that the temperature of the melt in the molten pool gradually increased, which led to an increase in the tension gradient on the surface of the molten poor dominated by the temperature gradient. The higher the tension gradient on the molten pool surface is, the more vigorously the convection of the melts in the molten pool, which causes the surface quality gradually becomes worse after solidification and crystallization.

The substrate structure in the bioceramic coating of sample No. 112 exhibits as cellular crystals, on which exists white fine particles and locally exists aggregated white clusters of particles. The structure of the bioceramic coating is compact. There are fewer gaps in the bioceramic coating.

More gaps start to appear in the bioceramic coating of sample No. 113. Upon careful observation, some white ultrafine microparticles distributed in the bioceramic coating can be seen. With the energy spectrum and electron microprobe analysis, the white ultrafine microparticles are determined to be mainly Ti and Ca enriched oxides. The existence of the white ultrafine microparticles can improve the toughness of the bioceramic coating.

Even more gaps appear in the microstructure of the bioceramic coating of sample No. 114. The compactness of the microstructure became worse.

Some gaps in the bioceramic coating of sample No. 115 has linked up with each other, forming large holes or cracks. The structure inevitably lowers the mechanical properties of the bioceramic coating.

In view of the above, along with an increase in the output power P, the structural compactness of the bioceramic coating lowers, because the sintering temperature of the ceramics increases due to the increase of the output power. Along with an increase in the sintering temperature, the crystal grains forming the ceramics gradually grow gradually. At the same time, angularities of the crystal grains become smooth and small crystal grains bonded to each other to form larger crystal grains. At this moment glassy liquid phase at the grain boundary fills the gaps among the crystal grains and bonds small crystal grains. Small crystal grains grow further and glassy liquid phase formed along with the increase in temperature further fills the gaps. As such, the growth of crystal grains and filling of the liquid phase recycle continuously and finally form ceramics by sintering.

Different from conventional sintering technologies, the laser cladding process is a rapid heating and rapid cooling process. When the output power is relatively high, i.e., the sintering temperature is relatively high, the particle size of the formed crystal grains is relatively large and the gaps formed due to failure to be filled by the liquid phase is relatively large as well. On the other hand, when the output power is relatively high, the thermal stress produced during the sintering process is relatively high, which would readily result in relatively large holes and cracks. The bioceramic coating of the present application is required to have certain porosity to enable bone tissues growing into the holes.

According to the above experimental results, when the output power P=2.5 kW, the surface of the prepared ceramics has certain compactness as well as certain porosity. Therefore, the output power P=2.5 kW is an optimal technological parameter.

(2) Effects of Output Power on Porosity of Composite Ceramic Coating

With IAS-4 quantitative image analysis system, planar porosity of bioceramic coatings of sample Nos. 112-115 was assayed, respectively. The results are shown in Table 2.

The specific procedures are described as follows. First of all, images of the bioceramic coating were collected. Gray value images were treated with shadow correction, image enhancement and the like in order to observe the gaps more clearly. Secondly, image thresholding segmentation was carried out. The area percent of the gaps was measured after binary image processing was conducted. Finally, porosities at different locations on the bioceramic coating were measured. The mean value of the porosities was calculated.

TABLE 2

Test Results of Porosities (%) of Different Samples

| | Sample No. | | | |
|---|---|---|---|---|
| | 112 | 113 | 114 | 115 |
| Porosity (%) | 5 | 7 | 17 | 21 |

According to the results shown in Table 2, along with an increase in the output power P, the porosity in the bioceramic coating increases gradually. When P=2.3 kW, as in sample No. 112, the porosity is the smallest. When P=2.9 kW, as in sample No. 115, the porosity in the bioceramic coating is the largest.

Microhardness of bioceramic coatings of sample Nos. 112 and 115 were measured, respectively. The result showed that the microhardness of bioceramic coating of sample No. 112 is larger than that of sample No. 115 because the structure of the bioceramic coating of sample No. 112 is compact and the porosity thereof is low. In contrast, the structure of the bioceramic coating of sample No. 115 is not compact and the porosity thereof is higher, which inevitably leads to a decrease in microhardness of the bioceramic coating. Therefore, regardless of porosity or hardness, the output power P=2.5 kW is an optimal parameter.

2. Determination of Scanning Rate V

The output power was fixed while the scanning rate was changed. The test scheme was designed as shown in Table 3.

TABLE 3

Technological Parameters of Broadband Laser Cladding Gradient Bioceramic Coating

| Sample No. | Output Power P (kW) | Scanning Rate V (mm/min) | Spot Size D (mm × mm) |
|---|---|---|---|
| 211 | 2.5 | 120 | 16 × 2 |
| 212 | 2.5 | 130 | 16 × 2 |
| 213 | 2.5 | 140 | 16 × 2 |
| 214 | 2.5 | 150 | 16 × 2 |

According to the results, among the samples tested, the bioceramic coating sample No. 211 has the largest gaps, in which some gaps linked up with each other to form a line, leading to the worst structural compactness of the bioceramic coating. Meanwhile, among the samples tested, the bioceramic coating sample No. 214 has the smallest gaps and the best structural compactness.

Upon determining the optimal output power, the structure and morphology of the prepared bioceramic coatings improved significantly. The effect of the scanning rate on the surface morphology of the ceramics is not so remarkable as that of the output power. Along with an increase in scanning rate, the structural compactness of the ceramics increases while the porosity of the ceramics decreases. Due to an increase in scanning rate, the residence time of light beams is relatively short, i.e., the sintering time becomes shortened. The crystal grains were cooled rapidly before growing such that the crystal grains were fined and the compactness of the crystal grains was increased. Moreover, when the scanning rate is relatively high, the power density on the surface of the materials becomes lower, resulting in a decrease in thermal stress such that the resultant holes and cracks would be reduced. Therefore, the increase in scanning rate will result in the increase in the compactness, the strength and the hardness. When the scanning rate V=150 mm/min, the compactness of the ceramics is relatively high and the bonding between the ceramics and the substrate is good.

In view of the above study results and analysis, the optimal technological parameters of broadband laser cladding are laser output power P=2.5 kW, scanning rate V=150 mm/min, and spot size D=16 mm×2 mm.

Implant Tests in Mature Dog's Femurs

The bioceramic composite coatings were manufactured into strip samples in 12 mm×3 mm×3 mm. The samples were subject to high temperature steam sterilization over 30 min at 126° C. Three mature and healthy dogs each with a weight of about 25 kg were selected. After anaesthetized, each of the three dogs was implanted with five samples, respectively, in the left and right femurs. From proximal part to the distal part of the femurs, the samples were in turn designated as 1#, 2#, 3#, 4# and 5#. The implant durations were one and a half months, three months and six months, respectively. Over each duration a duplicate of each sample was implanted. The dogs were sacrificed without suffering before removing the samples. The femoral parts in which samples were implanted were removed, fixed in 20% formalin, embedded with PMMA, sectioned and stained with Toluidine Blue. The sectioned tissues were observed with low power and high power microscopes.

Example 1

Gradient Bioceramic Coating

The gradient bioceramic coating was prepared with 60 to 0% by weight of powdery titanium having a particle size of 40 µm and 40 to 100% by weight of powdery composite ceramics having a particle size of 36 µm, wherein the powdery composite ceramics were prepared by adding 0.6% by weight of a rare earth oxide $CeO_2$ having a particle size of 4 µm into powdery ceramics which are obtained by mixing 78% by weight of $CaHPO_4.2H_2O$ and 22% by weight of $CaCO_3$.

A first gradient layer prepressed on the surface of a titanium alloy TC4 was prepared by mixing and grinding 60% by weight of powdery titanium and 40% by weight of powdery composite ceramics. A second gradient layer was prepared by mixing and grinding 30% by weight of powdery titanium and 70% by weight of powdery composite ceramics. A third gradient layer was prepared by mixing and grinding 100% by weight of powdery composite ceramics.

Broadband Laser Cladding Method of Making the Gradient Bioceramic Coating

The powdery ceramics and a rare earth oxide $CeO_2$ were mixed and ground over 3 hours to give a first mixture. The first mixture and powdery titanium were mixed and ground over 3 hours for thorough mixing to give a coating powder. The obtained coating powder was then mixed with 3 mL of soya alkyd, and the resulting mixture was prepressed on the surface of a titanium alloy TC4 with a pressure of 50 kg/cm². The thickness of the prepressed coating layer was 0.5 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.5 kW of output power P, 150 mm/min of scanning rate V, and 16 mm×2 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 2

Gradient Bioceramic Coating

The gradient bioceramic coating was prepared with 60 to 0% by weight of powdery titanium having a particle size of 20 µm, and 40 to 100% by weight of powdery composite ceramics having a particle size of 30 µm, wherein the powdery composite ceramics are prepared by adding 0.4% by weight of a rare earth oxide $Y_2O_3$ having a particle size of 1 µm into powdery ceramics which are obtained by mixing 72% by weight of $CaHPO_4.2H_2O$ and 28% by weight of $CaCO_3$.

Each gradient layer prepressed on the surface of a titanium alloy TC4 was identical to that in Example 1.

Broadband Laser Cladding Method of Making the Gradient Bioceramic Coating

The powdery ceramics and a rare earth oxide $Y_2O_3$ were mixed and ground over 3 hours to give a first mixture. The first mixture and powdery titanium were mixed and ground over 3 hours for thorough mixing to give a coating powder. The obtained coating powder was then mixed with 3 mL of soya alkyd, and the resulting mixture was prepressed on the surface of a titanium alloy TC4 with a pressure of 50 kg/cm². The thickness of the prepressed coating layer was 0.4 mm. The broadband laser cladding was carried out with TJ-HL-5000 5 kW $CO_2$ lasers, TJ-LTM-VI five-axis three axes linkage laser processing numerical control machine and KF-6 laser broadband scan mirror. The technological parameters of broadband laser cladding are 2.1 kW of output power P, 120 mm/min of scanning rate V, and 16 mm×1 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 3

Gradient Bioceramic Coating

The gradient bioceramic coating was prepared with 60 to 0% by weight of powdery titanium having a particle size of 80 μm and 40 to 100% by weight of powdery composite ceramics having a particle size of 50 μm, wherein the powdery composite ceramics are prepared by adding 0.8% by weight of a rare earth oxide $La_2O_3$ having a particle size of 5 μm into powdery ceramics which are obtained by mixing 80% by weight of $CaHPO_4 \cdot 2H_2O$ and 20% by weight of $CaCO_3$.

Each gradient layer prepressed on the surface of a titanium alloy TC4 was identical to that in Example 1.

Broadband Laser Cladding Method of Making the Gradient Bioceramic Coating

The powdery ceramics and a rare earth oxide $La_2O_3$ were mixed and ground over 3 hours to give a first mixture. The first mixture and powdery titanium were mixed and ground over 3 hours for thorough mixing to give a coating powder. The obtained coating powder was then mixed with 3 mL of soya alkyd, and the resulting mixture was prepressed on the surface of a titanium alloy TC4 with a pressure of 50 kg/cm². The thickness of the prepressed coating layer was 0.6 mm. The broadband laser cladding was carried out with TJ-HL-5000 5 kW $CO_2$ lasers, TJ-LTM-VI five-axis three axes linkage laser processing numerical control machine and KF-6 laser broadband scan mirror. The technological parameters of broadband laser cladding are 2.9 kW of output power P, 200 mm/min of scanning rate V, and 30 mm×4 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 4

The gradient bioceramic coating prepared in Example 2 (the coating comprises 0.4% of $Y_2O_3$) and a gradient bioceramic coating comprising no $Y_2O_3$ were implanted into femurs of a mature and healthy dog (using the method described in the Implant Tests in Mature Dog's Femurs in the present application). No physiological responses such as allergy, rejection and pathologic changes were observed at week 4, week 8 and week 24. No symptoms such as obvious fibrous capsules, chronic inflammation, degeneration of tissue morphology, and tissue necrosis were observed on the tissue sections. The gradient bioceramic coating comprising 0.4% of $Y_2O_3$ was bonded to new bone tissues at week 4 and there were no gaps between the bone tissues and the coating. The gradient bioceramic coating comprising no $Y_2O_3$ was not bonded to new bone tissues even after growing for 24 weeks.

Comparative Example 1

The gradient bioceramic coating prepared in Chinese patent application No. 200510200011.5 (the coating comprises 0.4% of $Y_2O_3$) was implanted into femurs of a mature and healthy dog. No physiological responses such as allergy, rejection and pathologic changes were observed at week 6, week 12 and week 24. No symptoms such as obvious fibrous capsules, chronic inflammation, degeneration of tissue morphology, and tissue necrosis were observed on the tissue sections. X-ray films showed that the thickness of hyperosteogeny increased gradually and the ceramic coating bonded to new bone tissues at week 6.

The above test results demonstrate that the bioceramic coating of the present application has better bioactivity and biocompatibility. The duration for bonding to bone tissues can be decreased by about 2 weeks.

Theoretically speaking, the higher content of powdery titanium is in the first gradient layer in the bioceramic coating, the better physicochemical compatibility exhibits between the coating and the titanium alloy TC4. However, compared with the bioceramic coating of Chinese patent application No. 200510200011.5, the content of powdery titanium in the first gradient layer in the bioceramic coating of the present application is decreased by 10%. The test results show that where the content of titanium is 60%, the bonding between the coating and the substrate is still a metallurgical bonding and the interfacial bonding strength between the coating and the substrate is higher. In view of the above, this ratio does not constitute an influence on the physicochemical compatibility between the coating and the titanium alloy TC4.

In addition, since the content of powdery titanium in the third gradient layer in the bioceramic coating of Examples 1-3 is zero, the content of hydroxyapatite (HA) produced during the laser cladding process is relatively high. The test results show that the content of pure HA produced during laser cladding 100% of powdery composite ceramics is about 20%, such that the content of HA in the bioceramic coating is higher. Therefore, the bioactivity and biocompatibility of the bioceramic coating of the present application are significantly higher compared with that of Chinese patent application No. 200510200011.5.

Compared with the state of the prior art, the present application utilizes broadband laser cladding techniques and more reasonable gradient design so that the obtained bioceramic coating has less cracks or holes, higher hardness, and better toughness. No amorphous phases exist in the coating. Moreover, because the content of powdery titanium in the third gradient layer which contacts with the human body is zero while the content of HA is higher, the bioactivity and biocompatibility of the obtained product are significantly increased. Therefore, the obtained product can be used in restoration of human femoral necrosis, hip joint or tooth defects and would not induce a rejection. The restoration period of the obtained product is shorter (compared with that of the bioceramic coating of Chinese patent application No. 200510200011.5, the restoration period is shortened by about 1 to 3 weeks depending on specific conditions of an individual).

The effects of the addition of a rare earth oxide into the powdery ceramics of Examples 1-3 are to catalytically synthesize hydroxyapatite and β-calcium phosphate during the laser cladding process, increase the mechanical properties of the bioceramic coating, and decrease the cracking sensitivity of the bioceramic coating. The bioceramic coating comprising a rare earth oxide (e.g., $CeO_2$ or $La_2O_3$) also has the anticoagulation effects and can prevent carcinogenesis. Moreover, because there are more micropores formed on the surface of the coating, more channels are provided for the bone tissues to grow into the coating.

Example 5

Gradient Bioceramic Coating

The gradient bioceramic coating was prepared with 60 to 0% by weight of powdery titanium having a particle size of 40 μm, 40 to 70% by weight of powdery composite ceramics having a particle size of 36 μm, and 0 to 50% by weight of hydroxyapatite having a particle size of 15 μm, wherein the powdery composite ceramics were prepared by adding 0.6% by weight of a rare earth oxide $Y_2O_3$ having a particle size of 4 μm into powdery ceramics which are obtained by mixing 78% by weight of $CaHPO_4.2H_2O$ and 22% by weight of $CaCO_3$.

A first gradient layer prepressed on the surface of a titanium alloy TC4 was prepared by mixing and grinding 60% by weight of powdery titanium and 40% by weight of powdery composite ceramics. A second gradient layer was prepared by mixing and grinding 30% by weight of powdery titanium and 70% by weight of powdery composite ceramics. A third gradient layer was prepared by mixing and grinding 50% by weight of powdery composite ceramics and 50% by weight of hydroxyapatite (HA).

Broadband Laser Cladding Method of Making the Gradient Bioceramic Coating

The powdery ceramics and a rare earth oxide $Y_2O_3$ were mixed and ground over 3 hours to give a first mixture. The first mixture and powdery titanium were mixed and ground over 3 hours for thorough mixing to give a first coating powder. The powdery ceramics and a rare earth oxide $Y_2O_3$ were mixed and ground over 3 hours to give a second mixture. The second mixture and hydroxyapatite were mixed and ground over 3 hours for thorough mixing to give a second coating powder. The obtained first coating powder was mixed with 3 mL of soya alkyd, and the resulting mixture was prepressed on the surface of a titanium alloy TC4 with a pressure of 50 kg/cm². The thickness of the prepressed coating layer was 0.5 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.5 kW of output power P, 150 mm/min of scanning rate V, and 16 mm×2 mm of spot size D. First of all, a first gradient layer was cladded on the surface of a titanium alloy TC4 and then cleaned the residues on the surface and washed the surface. The obtained first coating powder was prepressed on the surface of the titanium alloy TC4. A second gradient layer was cladded on the surface of the titanium alloy TC4 and then cleaned the residues on the surface and washed the surface. The obtained second coating powder was prepressed on the surface of the titanium alloy TC4. A third gradient layer was cladded on the surface of the titanium alloy TC4 to give a bioceramic coating on the surface of the titanium alloy TC4.

Example 6

Gradient Bioceramic Coating

The gradient bioceramic coating was prepared with 60 to 0% by weight of powdery titanium having a particle size of 20 μm, 40 to 70% by weight of powdery composite ceramics having a particle size of 30 μm, and 0 to 50% by weight of hydroxyapatite having a particle size of 10 μm, wherein the powdery composite ceramics are prepared by adding 0.4% by weight of a rare earth oxide $CeO_2$ having a particle size of 1 μm into powdery ceramics which are obtained by mixing 72% by weight of $CaHPO_4.2H_2O$ and 28% by weight of $CaCO_3$.

Each gradient layer prepressed on the surface of a titanium alloy TC4 was identical to that in Example 5.

Broadband Laser Cladding Method of Making the Gradient Bioceramic Coating

The powdery ceramics and a rare earth oxide $CeO_2$ were mixed and ground over 3 hours to give a first mixture. The first mixture and powdery titanium were mixed and ground over 3 hours for thorough mixing to give a first coating powder. The powdery ceramics and a rare earth oxide $CeO_2$ were mixed and ground over 3 hours to give a second mixture. The second mixture and hydroxyapatite were mixed and ground over 3 hours for thorough mixing to give a second coating powder. The obtained first coating powder was mixed with 1 mL of soya alkyd, and the resulting mixture was prepressed on the surface of a titanium alloy TC4 with a pressure of 50 kg/cm². The thickness of the prepressed coating layer was 0.54 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.1 kW of output power P, 120 mm/min of scanning rate V, and 16 mm×1 mm of spot size D. First of all, a first gradient layer was cladded on the surface of a titanium alloy TC4 and then cleaned the residues on the surface and washed the surface. The obtained first coating powder was prepressed on the surface of the titanium alloy TC4. A second gradient layer was cladded on the surface of the titanium alloy TC4 and then cleaned the residues on the surface and washed the surface. The obtained second coating powder was prepressed on the surface of the titanium alloy TC4. A third gradient layer was cladded on the surface of the titanium alloy TC4 to give a bioceramic coating on the surface of the titanium alloy TC4.

Example 7

Gradient Bioceramic Coating

The gradient bioceramic coating was prepared with 60 to 0% by weight of powdery titanium having a particle size of 80 μm, 40 to 70% by weight of powdery composite ceramics having a particle size of 50 μm, and 0 to 50% by weight of hydroxyapatite having a particle size of 30 μm, wherein the powdery composite ceramics are prepared by adding 0.8% by weight of a rare earth oxide $La_2O_3$ having a particle size of 5

μm into powdery ceramics which are obtained by mixing 80% by weight of $CaHPO_4 \cdot 2H_2O$ and 20% by weight of $CaCO_3$.

Each gradient layer prepressed on the surface of a titanium alloy TC4 was identical to that in Example 5.

Broadband Laser Cladding Method of Making the Gradient Bioceramic Coating

The powdery ceramics and a rare earth oxide $La_2O_3$ were mixed and ground over 3 hours to give a first mixture. The first mixture and powdery titanium were mixed and ground over 3 hours for thorough mixing to give a first coating powder. The powdery ceramics and a rare earth oxide $La_2O_3$ were mixed and ground over 3 hours to give a second mixture. The second mixture and hydroxyapatite were mixed and ground over 3 hours for thorough mixing to give a second coating powder. The obtained first coating powder was mixed with 5 mL of soya alkyd, and the resulting mixture was prepressed on the surface of a titanium alloy TC4 with a pressure of 50 kg/cm². The thickness of the prepressed coating layer was 0.6 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.9 kW of output power P, 200 mm/min of scanning rate V, and 30 mm×4 mm of spot size D. First of all, a first gradient layer was cladded on the surface of a titanium alloy TC4 and then cleaned the residues on the surface and washed the surface. The obtained first coating powder was prepressed on the surface of the titanium alloy TC4. A second gradient layer was cladded on the surface of the titanium alloy TC4 and then cleaned the residues on the surface and washed the surface. The obtained second coating powder was prepressed on the surface of the titanium alloy TC4. A third gradient layer was cladded on the surface of the titanium alloy TC4 to give a bioceramic coating on the surface of the titanium alloy TC4.

Example 8

The gradient bioceramic coating prepared in Example 5 (the coating comprises 0.6% of $Y_2O_3$) and a gradient bioceramic coating comprising no $Y_2O_3$ were implanted into femurs of a mature and healthy dog (using the method described in the Implant Tests in Mature Dog's Femurs in the present application). No physiological responses such as allergy, rejection and pathologic changes were observed at week 1, week 4 and week 8. No symptoms such as obvious fibrous capsules, chronic inflammation, degeneration of tissue morphology, and tissue necrosis were observed on the tissue sections. The gradient bioceramic coating comprising 0.6% of $Y_2O_3$ was bonded to new bone tissues at week 1 and there were no gaps between the bone tissues and the coating. The gradient bioceramic coating comprising no $Y_2O_3$ was not bonded to new bone tissues even after growing for 8 weeks.

Comparative Example 2

The gradient bioceramic coating prepared in Chinese patent application No. 200510200011.5 (the coating comprises 0.6% of $Y_2O_3$) was implanted into femurs of a mature and healthy dog. No physiological responses such as allergy, rejection and pathologic changes were observed at week 6, week 12 and week 24. No symptoms such as obvious fibrous capsules, chronic inflammation, degeneration of tissue morphology, and tissue necrosis were observed on the tissue sections. X-ray films showed that the thickness of hyperosteogeny increased gradually and the ceramic coating bonded to new bone tissues at week 6.

The above test results demonstrate that the bioceramic coating of the present application has better bioactivity and biocompatibility. The duration for bonding to bone tissues can be decreased by about 5 weeks.

Theoretically speaking, the higher content of powdery titanium is in the first gradient layer in the bioceramic coating, the better physicochemical compatibility exhibits between the coating and the titanium alloy TC4. However, compared with the bioceramic coating of Chinese patent application No. 200510200011.5, the content of powdery titanium in the first gradient layer in the bioceramic coating of the present application is decreased by 10%. The test results show that where the content of titanium is 60%, the bonding between the coating and the substrate is still a metallurgical bonding and the interfacial bonding strength between the coating and the substrate is higher. In view of the above, this ratio does not constitute an influence on the physicochemical compatibility between the coating and the titanium alloy TC4.

In addition, since the content of powdery titanium in the third gradient layer in the bioceramic coating of Examples 5-7 is zero, the content of hydroxyapatite (HA) produced during the laser cladding process is relatively high. The addition of 50% of HA results in an even higher content of HA in the coating. Therefore, the bioactivity and biocompatibility of the bioceramic coating of the present application are significantly higher compared with that of Chinese patent application No. 200510200011.5. The results of a series of tests show that the content of pure HA produced during laser cladding 100% of powdery composite ceramics is about 20%, while the content of pure HA produced during laser cladding 50% of powdery composite ceramics plus 50% of HA can reach about 60%.

Compared with the state of the prior art, the present application utilizes broadband laser cladding techniques and more reasonable gradient design so that the obtained bioceramic coating has less cracks or holes, higher hardness, and better toughness. No amorphous phases exist in the coating. Moreover, because the content of powdery titanium in the third gradient layer which contacts with the human body is zero while the content of HA is higher, the bioactivity and biocompatibility of the obtained product are significantly increased. Therefore, the obtained product can be used in restoration of human femoral necrosis, hip joint or tooth defects and would not induce a rejection. The restoration period of the obtained product is shorter (compared with that of the bioceramic coating of Chinese patent application No. 200510200011.5, the restoration period is shortened by about 3 to 5 weeks depending on specific conditions of an individual).

The effects of the addition of a rare earth oxide into the powdery ceramics of Examples 5-7 are to catalytically synthesize hydroxyapatite and β-calcium phosphate during the laser cladding process, increase the mechanical properties of the bioceramic coating, and decrease the cracking sensitivity of the bioceramic coating. The bioceramic coating comprising a rare earth oxide (e.g., $CeO_2$ or $La_2O_3$) also has the anticoagulation effects and can prevent carcinogenesis. Moreover, because there are more micropores formed on the surface of the coating, more channels are provided for the bone tissues to grow into the coating.

Example 9

Gradient Bioceramic Coating Comprising $CeO_2$

The gradient bioceramic coating was prepared with 70 to 10 kg of powdery titanium having a particle size of 40 μm, and 30 to 90 kg of powdery composite ceramics having a particle size of 36 μm, wherein the powdery composite ceramics were prepared by adding 0.6 kg of a rare earth oxide $CeO_2$ having a particle size of 4 μm into powdery ceramics which are obtained by mixing 78 kg of $CaHPO_4 \cdot 2H_2O$ and 22 kg of $CaCO_3$.

A first gradient layer prepressed on the surface of a titanium alloy TC4 was prepared by mixing and grinding 70 kg of powdery titanium and 30 kg of powdery composite ceramics. A second gradient layer was prepared by mixing and grinding 40 kg of powdery titanium and 60 kg of powdery composite ceramics. A third gradient layer was prepared by mixing and grinding 10 kg of powdery titanium and 90 kg of powdery composite ceramics.

Method of Making the Gradient Bioceramic Coating Comprising $CeO_2$

The powdery ceramics and a rare earth oxide $CeO_2$ were mixed and ground over 3 hours to give a first mixture. The first mixture and powdery titanium were mixed and ground over 3 hours for thorough mixing to give a coating powder. The obtained coating powder was mixed with 3 mL of soya alkyd, and the resulting mixture was prepressed on the surface of a titanium alloy TC4 with a pressure of 50 kg/cm². The thickness of the prepressed coating layer was 0.5 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.5 kW of output power P, 150 mm/min of scanning rate V, and 16 mm×2 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 10

Gradient Bioceramic Coating Comprising $CeO_2$

The gradient bioceramic coating was prepared with 75 to 15 kg of powdery titanium having a particle size of 20 μm, and 35 to 85 kg of powdery composite ceramics having a particle size of 30 μm, wherein the powdery composite ceramics were prepared by adding 0.4 kg of a rare earth oxide $CeO_2$ having a particle size of 1 μm into powdery ceramics which are obtained by mixing 72 kg of $CaHPO_4 \cdot 2H_2O$ and 28 kg of $CaCO_3$.

A first gradient layer prepressed on the surface of a titanium alloy TC4 was prepared by mixing and grinding 75 kg of powdery titanium and 25 kg of powdery composite ceramics. A second gradient layer was prepared by mixing and grinding 45 kg of powdery titanium and 55 kg of powdery composite ceramics. A third gradient layer was prepared by mixing and grinding 15 kg of powdery titanium and 85 kg of powdery composite ceramics.

Method of Making the Gradient Bioceramic Coating Comprising $CeO_2$

The powdery ceramics and a rare earth oxide $CeO_2$ were mixed and ground over 3 hours to give a first mixture. The first mixture and powdery titanium were mixed and ground over 3 hours for thorough mixing to give a coating powder. The obtained coating powder was mixed with 1 mL of soya alkyd, and the resulting mixture was prepressed on the surface of a titanium alloy TC4 with a pressure of 50 kg/cm². The thickness of the prepressed coating layer was 0.4 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.0 kW of output power P, 100 mm/min of scanning rate V, and 16 mm×1 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 11

Gradient Bioceramic Coating Comprising $CeO_2$

The gradient bioceramic coating was prepared with 80 to 20 kg of powdery titanium having a particle size of 80 μm, and 20 to 80 kg of powdery composite ceramics having a particle size of 50 μm, wherein the powdery composite ceramics were prepared by adding 0.8 kg of a rare earth oxide $CeO_2$ having a particle size of 5 μm into powdery ceramics which are obtained by mixing 80 kg of $CaHPO_4 \cdot 2H_2O$ and 20 kg of $CaCO_3$.

A first gradient layer prepressed on the surface of a titanium alloy TC4 was prepared by mixing and grinding 80 kg of powdery titanium and 20 kg of powdery composite ceramics. A second gradient layer was prepared by mixing and grinding 50 kg of powdery titanium and 50 kg of powdery composite ceramics. A third gradient layer was prepared by mixing and grinding 20 kg of powdery titanium and 80 kg of powdery composite ceramics.

Method of Making the Gradient Bioceramic Coating Comprising $CeO_2$

The powdery ceramics and a rare earth oxide $CeO_2$ were mixed and ground over 3 hours to give a first mixture. The first mixture and powdery titanium were mixed and ground over 3 hours for thorough mixing to give a coating powder. The obtained coating powder was mixed with 5 mL of soya alkyd, and the resulting mixture was prepressed on the surface of a titanium alloy TC4 with a pressure of 50 kg/cm². The thickness of the prepressed coating layer was 0.6 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 3.0 kW of output power P, 200 mm/min of scanning rate V, and 30 mm×4 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 12

The gradient bioceramic coating prepared in Example 9 (the coating comprises 0.6% of $CeO_2$) and a gradient bioceramic coating comprising no $CeO_2$ were implanted into femurs of a mature and healthy dog (using the method described in the Implant Tests in Mature Dog's Femurs in the present application). No physiological responses such as allergy, rejection and pathologic changes were observed at week 6, week 12 and week 24. No symptoms such as obvious fibrous capsules, chronic inflammation, degeneration of tissue morphology, and tissue necrosis were observed on the tissue sections. The gradient bioceramic coating comprising 0.6% of $CeO_2$ was bonded to new bone tissues at week 6 and there were no gaps between the bone tissues and the coating. The gradient bioceramic coating comprising no $CeO_2$ was not bonded to new bone tissues even after growing for 24 weeks. This shows that the gradient bioceramic coating comprising 0.6% of $CeO_2$ has good bioactivity and biocompatibility.

Compared with the state of the prior art, the bioceramic coatings of Examples 9-11 have less cracks or holes, higher hardness and better toughness. No amorphous phases exist in the coatings. The product can be implanted into the human body as a substitute for bone and bone joint. The product has the anticoagulation effects and can prevent carcinogenesis while would not induce a rejection.

The present application utilizes a concept of gradient design and uses broadband laser cladding techniques to directly clad $CaHPO_4.2H_2O+CaCO_3+Ti$ powder on the surface of a titanium alloy (i.e., one-step process) so as to increase the bonding strength of the interface and endow the coating with good biocompatibility. The Gaussian energy distribution of broadband laser becomes a rectangular energy distribution after being treated with broadband scan mirror such that the energy distribution becomes uniform. Such a rectangular energy distribution can make the temperature distribution of a molten pool uniform and make the temperature in the central area of the molten pool decreasing in a gradient manner such that the cracking sensitivity decreases. Moreover, the temperature gradient of the molten pool edges can form an appropriate surface tension field and play a role in stirring the melt so as to make alloy elements distribute uniformly. In addition, the width of the cladding can be increased and the lapping times can be reduced so that the productivity will be increased.

The addition of $CeO_2$ into the powdery ceramics in Example 9-11 plays a role in catalytically synthesize hydroxyapatite and β-calcium phosphate and the obtained bioceramic coating also has the anticoagulation effects and can prevent carcinogenesis. Furthermore, more micropores are formed on the surface of the bioceramic coating comprising $CeO_2$ than those formed on the surface of the bioceramic coating comprising $Y_2O_3$ such that more channels are provided for the bone tissues to grow into the coating.

Example 13

Gradient Bioceramic Coating Comprising $La_2O_3$

The gradient bioceramic coating was prepared with 70 to 10% by weight of powdery titanium having a particle size of 40 μm, and 30 to 90% by weight of powdery composite ceramics having a particle size of 36 μm, wherein the powdery composite ceramics were prepared by adding 0.6% by weight of a rare earth oxide $La_2O_3$ having a particle size of 4 μm into powdery ceramics which are obtained by mixing 78% by weight of $CaHPO_4.2H_2O$ and 22% by weight of $CaCO_3$.

A first gradient layer prepressed on the surface of a titanium alloy TC4 was prepared by mixing and grinding 70% by weight of powdery titanium and 30% by weight of powdery composite ceramics. A second gradient layer was prepared by mixing and grinding 40% by weight of powdery titanium and 60% by weight of powdery composite ceramics. A third gradient layer was prepared by mixing and grinding 10% by weight of powdery titanium and 90% by weight of powdery composite ceramics.

Method of Making the Gradient Bioceramic Coating Comprising $La_2O_3$

The powdery ceramics and a rare earth oxide $La_2O_3$ were mixed and ground over 3 hours to give a first mixture. The first mixture and powdery titanium were mixed and ground over 3 hours for thorough mixing to give a coating powder. The obtained coating powder was mixed with 3 mL of soya alkyd, and the resulting mixture was prepressed on the surface of a titanium alloy TC4 with a pressure of 50 kg/cm². The thickness of the prepressed coating layer was 0.5 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.5 kW of output power P, 150 mm/min of scanning rate V, and 16 mm×2 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 14

Gradient Bioceramic Coating Comprising $La_2O_3$

The gradient bioceramic coating was prepared with 75 to 15% by weight of powdery titanium having a particle size of 20 μm, and 25 to 85% by weight of powdery composite ceramics having a particle size of 30 μm, wherein the powdery composite ceramics were prepared by adding 0.4% by weight of a rare earth oxide $La_2O_3$ having a particle size of 1 μm into powdery ceramics which are obtained by mixing 72% by weight of $CaHPO_4.2H_2O$ and 28% by weight of $CaCO_3$.

A first gradient layer prepressed on the surface of a titanium alloy TC4 was prepared by mixing and grinding 75% by weight of powdery titanium and 25% by weight of powdery composite ceramics. A second gradient layer was prepared by mixing and grinding 45% by weight of powdery titanium and 55% by weight of powdery composite ceramics. A third gradient layer was prepared by mixing and grinding 15% by weight of powdery titanium and 85% by weight of powdery composite ceramics.

Method of Making the Gradient Bioceramic Coating Comprising $La_2O_3$

The powdery ceramics and a rare earth oxide $La_2O_3$ were mixed and ground over 3 hours to give a first mixture. The first mixture and powdery titanium were mixed and ground over 3 hours for thorough mixing to give a coating powder. The obtained coating powder was mixed with 1 mL of soya alkyd, and the resulting mixture was prepressed on the surface of a titanium alloy TC4 with a pressure of 50 kg/cm². The thickness of the prepressed coating layer was 0.4 mm. The broadband laser cladding was carried out with TJ-HL-5000 5 kW $CO_2$ lasers, TJ-LTM-VI five-axis three axes linkage laser processing numerical control machine, and KF-6 laser broadband scan mirror. The technological parameters of broadband laser cladding are 2.1 kW of output power P, 120 mm/min of scanning rate V, and 16 mm×1 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 15

Gradient Bioceramic Coating Comprising $La_2O_3$

The gradient bioceramic coating was prepared with 80 to 20% by weight of powdery titanium having a particle size of 80 μm, and 20 to 80% by weight of powdery composite ceramics having a particle size of 50 μm, wherein the powdery composite ceramics were prepared by adding 0.8% by weight of a rare earth oxide $La_2O_3$ having a particle size of 5 μm into powdery ceramics which are obtained by mixing 80% by weight of $CaHPO_4.2H_2O$ and 20% by weight of $CaCO_3$.

A first gradient layer prepressed on the surface of a titanium alloy TC4 was prepared by mixing and grinding 80% by weight of powdery titanium and 20% by weight of powdery composite ceramics. A second gradient layer was prepared by mixing and grinding 50% by weight of powdery titanium and 50% by weight of powdery composite ceramics. A third gradient layer was prepared by mixing and grinding 20% by weight of powdery titanium and 80% by weight of powdery composite ceramics.

Method of Making the Gradient Bioceramic Coating Comprising $La_2O_3$

The powdery ceramics and a rare earth oxide $La_2O_3$ were mixed and ground over 3 hours to give a first mixture. The first mixture and powdery titanium were mixed and ground over 3 hours for thorough mixing to give a coating powder. The obtained coating powder was mixed with 5 mL of soya alkyd, and the resulting mixture was prepressed on the surface of a titanium alloy TC4 with a pressure of 50 kg/cm². The thickness of the prepressed coating layer was 0.6 mm. The broadband laser cladding was carried out with TJ-HL-5000 5 kW $CO_2$ lasers, TJ-LTM-VI five-axis three axes linkage laser processing numerical control machine, and KF-6 laser broadband laser scan mirror. The technological parameters of broadband laser cladding are 2.9 kW of output power P, 200 mm/min of scanning rate V, and 30 mm×4 mm of spot size D. First of all, a first gradient layer was cladded on the surface of a titanium alloy TC4 and then cleaned the residues on the surface and washed the surface. The obtained coating powder was prepressed on the surface of the titanium alloy TC4. A second gradient layer was cladded on the surface of the titanium alloy TC4 and then cleaned the residues on the surface and washed the surface. The obtained coating powder was prepressed on the surface of the titanium alloy TC4. A third gradient layer was cladded on the surface of the titanium alloy TC4 to give a bioceramic coating on the surface of the titanium alloy TC4.

Example 16

The gradient bioceramic coating prepared in Example 14 (the coating comprises 0.4% of $La_2O_3$) and a gradient bioceramic coating comprising no $La_2O_3$ were implanted into femurs of a mature and healthy dog (using the method described in the Implant Tests in Mature Dog's Femurs in the present application). No physiological responses such as allergy, rejection and pathologic changes were observed at week 6, week 12 and week 24. No symptoms such as obvious fibrous capsules, chronic inflammation, degeneration of tissue morphology, and tissue necrosis were observed on the tissue sections. The gradient bioceramic coating comprising 0.6% of $CeO_2$ was bonded to new bone tissues at week 6 and there were no gaps between the bone tissues and the coating. The gradient bioceramic coating comprising no $La_2O_3$ was not bonded to new bone tissues even after growing for 24 weeks. This shows that the gradient bioceramic coating comprising 0.4% of $La_2O_3$ has good bioactivity and biocompatibility.

Compared with the state of the prior art, the bioceramic coatings of Examples 13-15 have less cracks or holes, higher hardness and better toughness. No amorphous phases exist in the coatings. The product can be implanted into the human body as a substitute for bone and bone joint. The product has the anticoagulation effects and can prevent carcinogenesis while would not induce a rejection.

The present application utilizes a concept of gradient design and uses broadband laser cladding techniques to directly clad $CaHPO_4.2H_2O+CaCO_3+Ti$ powder on the surface of a titanium alloy (i.e., one-step process) so as to increase the bonding strength of the interface and endow the coating with good biocompatibility. The Gaussian energy distribution of broadband laser becomes a rectangular energy distribution after being treated with broadband scan mirror such that the energy distribution becomes uniform. Such a rectangular energy distribution can make the temperature distribution of a molten pool uniform and make the temperature in the central area of the molten pool decreasing in a gradient manner such that the cracking sensitivity decreases. Moreover, the temperature gradient of the molten pool edges can form an appropriate surface tension field and play a role in stirring the melt so as to make alloy elements distribute uniformly. In addition, the width of the cladding can be increased and the lapping times can be reduced so that the productivity will be increased.

The addition of $La_2O_3$ into the powdery ceramics in Example 13-15 plays a role in catalytically synthesize hydroxyapatite and β-calcium phosphate and the obtained bioceramic coating also has the anticoagulation effects and can prevent carcinogenesis. Furthermore, more micropores are formed on the surface of the bioceramic coating comprising $La_2O_3$ than those formed on the surface of the bioceramic coating comprising $Y_2O_3$ such that more channels are provided for the bone tissues to grow into the coating.

These and other changes can be made in light of the above-detailed description. In general, in the following claims, the terms used should not be construed to be limiting to the specific embodiments disclosed in the specification and the claims, but should be construed to include all systems, devices and/or methods that operate in accordance with the claims. Accordingly, the invention is not limited by the disclosure, but instead its scope is to be determined entirely by the following claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A gradient bioceramic coating, wherein the gradient bioceramic coating is prepared with powdery titanium, powdery composite ceramics and hydroxyapatite, wherein the powdery composite ceramics is composed of powdery ceramics obtained by mixing $CaHPO_4 \cdot 2H_2O$ and $CaCO_3$, and a rare earth oxide, wherein the gradient bioceramic coating comprises a first gradient layer, a second gradient layer and a third gradient layer and wherein the first gradient layer and the second gradient layer are composed of powdery titanium and powdery composite ceramics, and the third gradient layer is composed of powdery composite ceramics and hydroxyapatite.

2. The gradient bioceramic coating of claim 1, wherein on the basis of weight percent, the gradient bioceramic coating is prepared with about 60 to 0% of powdery titanium, about 40 to 100% of powdery composite ceramics and about 0 to 50% of hydroxyapatite, wherein the powdery composite ceramics are composed of powdery ceramics obtained by mixing about 67 to 85% by weight of $CaHPO_4 \cdot 2H_2O$ and about 15 to 33% by weight of $CaCO_3$, and about 0.2 to 1.0% by weight of a rare earth oxide.

3. The gradient bioceramic coating of claim 1, wherein the particle size of the powdery titanium is in the range of about 10 to 90 μm, the particle size of the powdery composite ceramics is in the range of about 20 to 60 μm, the particle size of the hydroxyapatite is in the range of about 5 to 50 μm, and the particle size of the rare earth oxide is in the range of about 0.1 to 10 μm.

4. The gradient bioceramic coating of claim 3, wherein the particle size of the powdery titanium is about 40 μm, the particle size of the powdery composite ceramics is about 36 μm, the particle size of the hydroxyapatite is about 15 μm, and the particle size of the rare earth oxide is about 4 μm.

5. The gradient bioceramic coating of claim 1, wherein the rare earth oxide is selected from the group consisting of yttrium oxide ($Y_2O_3$), yttrium europium oxide (($Y,Eu)_2O_3$), europium oxide ($Eu_2O_3$), lanthanum oxide ($La_2O_3$), cerous oxide ($Ce_2O_3$), ceric oxide ($CeO_2$), terbium oxide ($Tb_4O_7$) (including cerium terbium oxide (($Ce, Tb)_xO_y$), lanthanum cerium terbium oxide (($La, Ce, Tb)_xO_y$), lanthanum phosphate activated by cerium and terbium: Ce(III), Tb(III)), samarium oxide ($Sm_2O_3$), neodminu oxide ($Nd_2O_3$), dysprosium oxide ($Dy_2O_3$), erbium oxide ($Er_2O_3$), ytterbium oxide ($Yb_2O_3$) and cerium zirconium oxide (($Ce,Zr)O_2$).

6. The gradient bioceramic coating of claim 5, wherein the rare earth oxide is selected from the group consisting of lanthanum oxide ($La_2O_3$), ceric oxide ($CeO_2$) and yttrium oxide ($Y_2O_3$).

* * * * *